United States Patent
Gono et al.

(10) Patent No.: US 8,491,469 B2
(45) Date of Patent: Jul. 23, 2013

(54) BIOLOGICAL MEASUREMENT APPARATUS, BIOLOGICAL OBSERVATION APPARATUS AND OPERATION METHOD FOR BIOLOGICAL MEASUREMENT APPARATUS

(75) Inventors: Kazuhiro Gono, Sagamihara (JP); Makoto Igarashi, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/021,142

(22) Filed: Feb. 4, 2011

(65) Prior Publication Data

US 2011/0275898 A1    Nov. 10, 2011

Related U.S. Application Data

(63) Continuation of application No. PCT/JP2010/058772, filed on May 24, 2010.

(30) Foreign Application Priority Data

Aug. 20, 2009   (JP) .................................. 2009-191369

(51) Int. Cl.
| | |
|---|---|
| *A61B 1/06* | (2006.01) |
| *A61B 1/12* | (2006.01) |
| *A61B 5/00* | (2006.01) |
| *A61B 18/18* | (2006.01) |
| *A61F 7/00* | (2006.01) |

(52) U.S. Cl.
USPC ............... 600/160; 600/158; 600/310; 606/3; 607/104

(58) Field of Classification Search
USPC ............... 600/160, 156, 158, 310, 407, 411, 600/476, 427; 700/228, 240; 348/61; 340/618, 340/619; 141/11, 1; 359/665; 606/3; 607/104
See application file for complete search history.

(56) References Cited

U.S. PATENT DOCUMENTS

| | | | | |
|---|---|---|---|---|
| 5,356,081 | A | * | 10/1994 | Sellar ................................ 241/1 |
| 5,609,563 | A | * | 3/1997 | Suzuki et al. ................. 600/118 |
| 5,836,941 | A | | 11/1998 | Yoshihara et al. |
| 6,332,092 | B1 | | 12/2001 | Deckert et al. |

(Continued)

FOREIGN PATENT DOCUMENTS

| | | |
|---|---|---|
| EP | 1 922 991 A1 | 5/2008 |
| JP | SHO 57-168654 | 10/1982 |

(Continued)

OTHER PUBLICATIONS

Abstract of International Publication No. WO 00/42912, dated Jul. 27, 2000.

*Primary Examiner* — John P Leubecker
*Assistant Examiner* — Ronald D Colque
(74) *Attorney, Agent, or Firm* — Scully, Scott, Murphy & Presser, P.C.

(57) ABSTRACT

A biological measurement apparatus includes: an endoscope including a treatment instrument insertion channel provided inside an insertion portion; a pump that delivers water into the treatment instrument insertion channel; an optical system, etc., that guide light from a light source that emits light in a predetermined wavelength band into the water delivered into the treatment instrument insertion channel; and a spectroscope that detects return light resulting from the light passing through the water, falling on and being reflected by an object and returning while passing through the water when the water is delivered from the pump.

8 Claims, 9 Drawing Sheets

U.S. PATENT DOCUMENTS

| | | | |
|---|---|---|---|
| 6,487,440 B2 * | 11/2002 | Deckert et al. | 600/476 |
| 2002/0049389 A1 * | 4/2002 | Abreu | 600/558 |
| 2002/0089586 A1 * | 7/2002 | Suzuki et al. | 348/68 |
| 2004/0039297 A1 * | 2/2004 | Abreu | 600/558 |
| 2005/0228229 A1 * | 10/2005 | Harris | 600/168 |
| 2006/0104859 A1 * | 5/2006 | Tribelsky | 422/24 |
| 2007/0016074 A1 * | 1/2007 | Abreu | 600/475 |
| 2007/0027391 A1 * | 2/2007 | Kohno | 600/427 |
| 2007/0142718 A1 * | 6/2007 | Abreu | 600/323 |
| 2007/0187632 A1 * | 8/2007 | Igarashi | 250/559.36 |
| 2007/0268489 A1 * | 11/2007 | Schwabe | 356/337 |
| 2008/0119694 A1 | 5/2008 | Lee | |
| 2008/0268486 A1 * | 10/2008 | Braig et al. | 435/14 |
| 2009/0000639 A1 * | 1/2009 | Tribelsky et al. | 134/1 |
| 2009/0326390 A1 * | 12/2009 | Belalcazar et al. | 600/486 |

FOREIGN PATENT DOCUMENTS

| | | |
|---|---|---|
| JP | 02-239858 | 9/1990 |
| JP | 07-171162 | 7/1995 |
| JP | 2002-520647 | 7/2002 |
| JP | 2002-535027 | 10/2002 |
| JP | 2008-061969 | 3/2008 |
| JP | 2008-178668 | 8/2008 |
| WO | WO 00/03272 | 1/2000 |

* cited by examiner

BIOLOGICAL MEASUREMENT APPARATUS, BIOLOGICAL OBSERVATION APPARATUS AND OPERATION METHOD FOR BIOLOGICAL MEASUREMENT APPARATUS

CROSS REFERENCE TO RELATED APPLICATION

This application is a continuation application of PCT/JP2010/058772 filed on May 24, 2010 and claims benefit of Japanese Application No. 2009-191369 filed in Japan on Aug. 20, 2009, the entire contents of which are incorporated herein by this reference.

BACKGROUND OF THE INVENTION

1. Field of the Invention

The present invention relates to a biological measurement apparatus, a biological observation apparatus and an operation method for the biological measurement apparatus, and specifically relates to a biological measurement apparatus, a biological observation apparatus and an operation method for the biological measurement apparatus, which use an endoscope and a liquid.

2. Description of the Related Art

Conventionally, for, e.g., disease diagnosis, biopsies in which a living tissue is extracted to conduct an examination have widely been conducted. Although biopsy is a method in which a living tissue itself is extracted to conduct an examination, optical biopsy methods have been proposed. In the optical biopsy methods, an examination is conducted by means of evaluating the state of a living tissue by applying light to the living tissue and measuring the light reflected by the living tissue, rather than extracting the living tissue.

For example, as disposed in Japanese Patent Application Laid-Open Publication No. 2002-535027, spectroscopy has been known as a system in which a probe including an optical fiber therein is inserted through a channel in an endoscope and is made to project from a distal end portion of an insertion portion of the endoscope to irradiate a tissue with light, thereby measuring the characteristics of the tissue. In the system, light from a light source is made to enter one end of the optical fiber and the light exits from a distal end of the probe projecting from the distal end portion of the insertion portion of the endoscope. Reflected light from the living tissue is received by one end of an optical fiber other than the optical fiber for emission. The light entering a distal end of the optical fiber for light reception enters a spectroscope through the optical fiber and is subjected to spectral measurement.

SUMMARY OF THE INVENTION

An aspect of the present invention enables provision of a biological measurement apparatus including: a liquid delivery apparatus that delivers a liquid into a tube portion provided inside or outside an insertion portion; a light guide section that guides light from a light source that emits light in a predetermined wavelength band into the liquid delivered into the tube portion; and a photodetection section that detects return light resulting from the light passing through the liquid, falling on and being reflected by an object and returning while passing through the liquid when the liquid is delivered from the liquid delivery apparatus.

An aspect of the present invention enables provision of an operation method for a biological measurement apparatus, including: delivering a liquid into a tube portion provided inside or outside an insertion portion, via a liquid delivery apparatus; guiding light from a light source that emits light in a predetermined wavelength band into the liquid delivered into the tube portion, via a light guide section; and detecting return light resulting from the light passing through the liquid, falling on and being reflected by an object and returning when the liquid is delivered into the tube portion, via a photodetection section.

An aspect of the present invention enables provision of a biological observation apparatus including: a liquid delivery section that delivers a liquid into a tube portion provided inside or outside an insertion portion; a light guide section that guides light from a light source that emits light in a predetermined wavelength band into the liquid delivered into the tube portion; an ejection section that ejects the light from the light guide section and the liquid to a target site; and an illumination section that illuminates at least the target site with at least a part of the light ejected from the ejection section, the illumination section being formed of the liquid.

DETAILED DESCRIPTION OF THE PREFERRED EMBODIMENT

Hereinafter, an embodiment of the present invention will be described with reference to the drawings.

Figure 1:
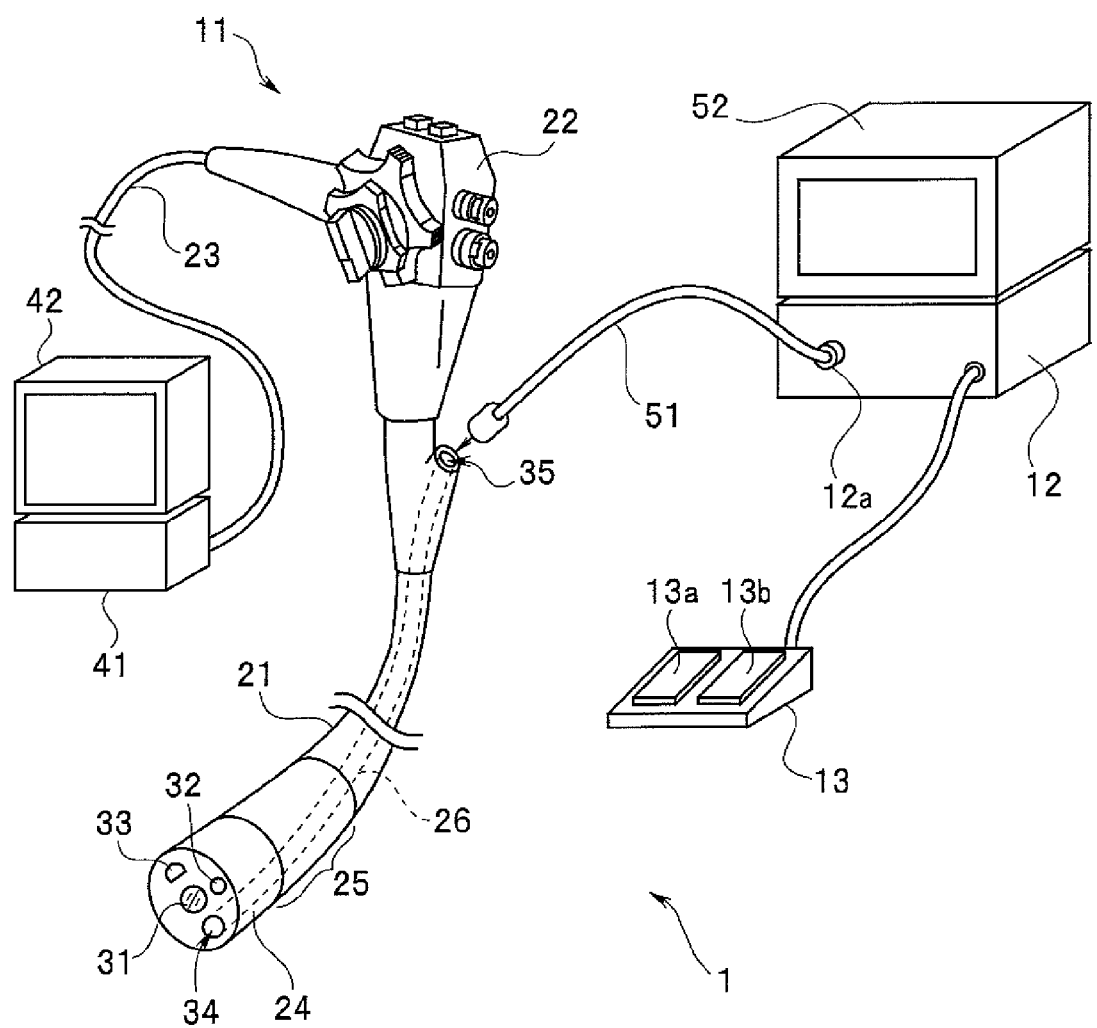
FIG. 1 is a configuration diagram illustrating a configuration of a biological measurement system according to an embodiment of the present invention.

First, a configuration of a biological measurement system according to the present embodiment will be described based on FIG. 1. FIG. 1 is a configuration diagram illustrating a configuration of a biological measurement system according to the present embodiment.

A biological measurement system 1, as a biological observation apparatus or a biological measurement apparatus, includes an endoscope 11, a main body apparatus 12 and a foot switch 13. The endoscope 11 includes an elongated insertion portion 21, an operation section 22 and a connection cable 23. A proximal end portion of the insertion portion 21 is connected to the operation section 22. A distal-end rigid portion 24 is provided at a distal end portion of the insertion portion 21, and a bending portion 25 is provided on the proximal end side of the distal-end rigid portion 24. Inside the insertion portion 21, a treatment instrument insertion channel 26 constituting a tube portion is arranged. The surfaces of the inner sides of the treatment instrument insertion channel 26 and a later-described connection tube 51 are provided with mirror-finished metal coating or a reflective material such as magnesium oxide, thereby reflecting light.

At a distal end portion thereof, an observation window 31 for an image pickup device such as a CCD, an illumination window 32 for illumination, and an air/water-delivery nozzle 33 for the observation window 31 and an opening portion 34 for the treatment instrument insertion channel 26. An opening portion for inserting a treatment instrument into the treatment instrument insertion channel 26, that is, a treatment instrument insertion opening 35 is provided in the operation section 22.

The connection cable 23 connected to the operation section 22 is connected to a camera control unit 41 including, e.g., an image processing section that processes an image obtained by the endoscope 11. The camera control unit 41 outputs video signals for displaying an endoscope image on a monitor 42. A surgeon can perform, e.g., observation of the inside of a body cavity while viewing the endoscope image outputted to the monitor.

The main body apparatus 12 includes a liquid delivery function and a spectral measurement function as described later. A configuration of the main body apparatus 12 will be described later. The endoscope 11 and the main body apparatus 12 can be connected via the connection tube 51, which is a tube for delivering a liquid from the main body apparatus 12 to the endoscope 11. One end of the connection tube 51 is fixedly or detachably connected to a water delivery connector 12a in the main body apparatus 12, and the other end is detachably connected to the treatment instrument insertion opening 35 of the endoscope 11.

A foot switch 13 is connected to the main body apparatus 12. As described later, the foot switch 13 here includes two pedals 13a and 13b. The pedal 13a is a switch to be pressed by a surgeon with a foot when the surgeon orders a cleaning operation, and the pedal 13b is a switch to be pressed by the surgeon with a foot when the surgeon orders a measurement operation. Each of the two switches is turned on when the switch is pressed by a foot, and is turned off when the foot is removed from the switch.

Also, a monitor 52 for displaying the results of biological measurement is connected to the main body apparatus 12.

As described later, a user can conduct an optical biopsy while operating the endoscope 11 and the foot switch 13.

Although the present embodiment is described in terms of an example in which water is used as a liquid used in an optical biopsy, e.g., normal saline or an acetic acid may be used for the liquid. In particular, an acetic acid provides an effect of improving visualization of the state of a mucous membrane surface.

Figure 2:
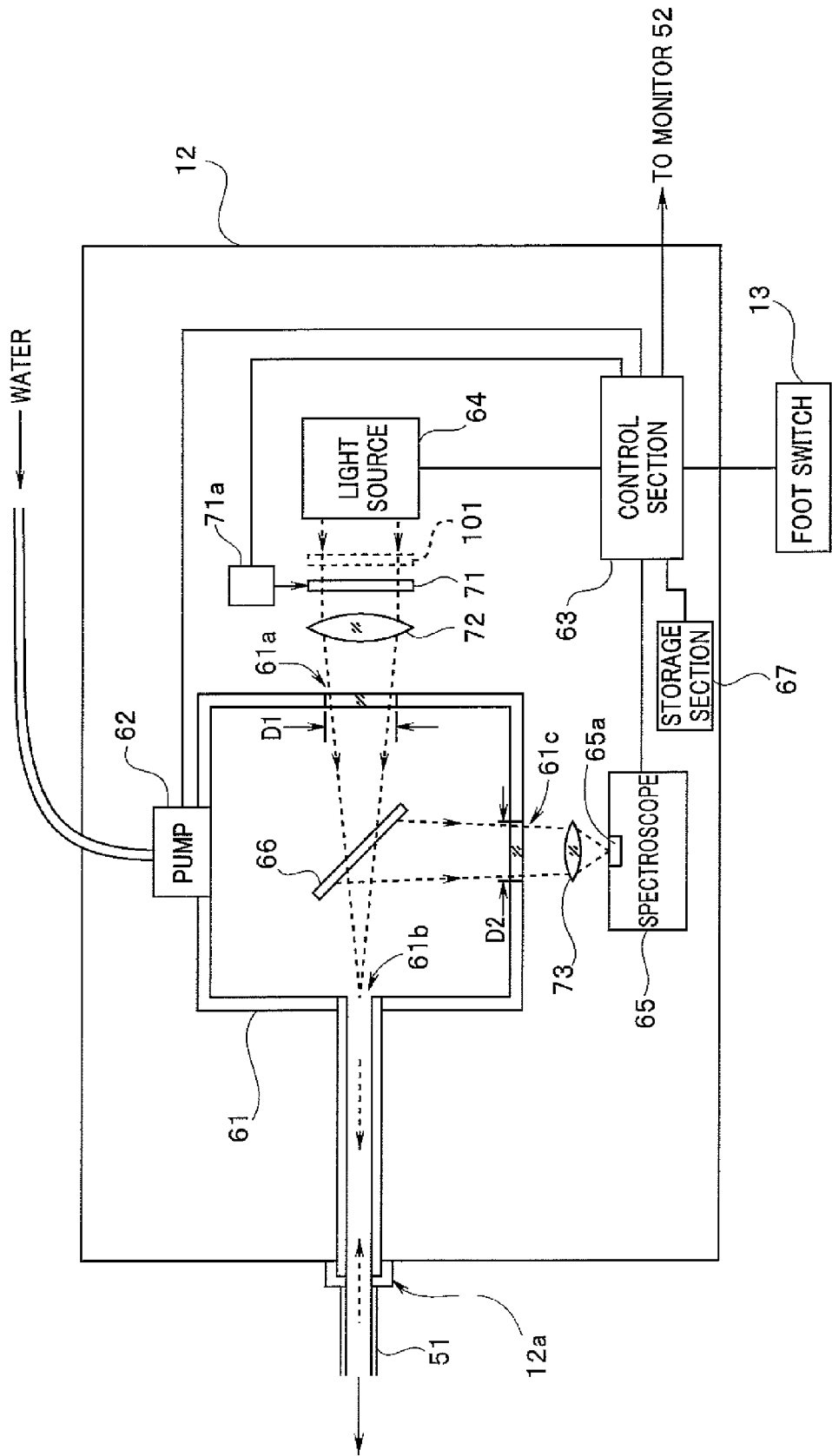
FIG. 2 is a diagram for illustrating an example configuration of a main body apparatus 12.

FIG. 2 is a diagram for illustrating an example configuration of the main body apparatus 12. The main body apparatus 12 includes a tank 61, a pump 62 connected to a water source such as a water feed tank, the pump 62 drawing water into the tank 61, a control section 63 including a central processing unit (CPU) and a memory, a light source 64, and a spectroscope 65, which is a photodetection section.

The control section 63, which is connected to the foot switch 13, receives on/off signals from the foot switch 13, and as described later, performs control of, e.g., the pump 62, the light source 64 and the spectroscope 65. The pump 62 and the tank 61 constitute a liquid delivery apparatus for delivering water into the treatment instrument insertion channel 26 constituting a tube portion. A storage section 67 for storing measurement data is connected to the control section 63.

The light source 64 is an apparatus that emits light in a predetermined wavelength band, and here, emits white color light including wavelengths of from 400 to 800 nm.

The light source 64 and the tank 61 are arranged so that the light emitted from the light source 64 advances toward an entrance window 61a provided in the tank 61 through a shutter 71 and an optical system 72 such as a lens.

The shape of the tank 61 may be a box shape or a cylindrical shape. A half mirror 66 as light separating means is provided in the tank 61. The half mirror 66 is a beam splitter that separates the light from the light source 64 and return light.

The entrance window 61a, the half mirror 66 and a discharge opening 61b for water are arranged so that the light entering the tank 61 from the entrance window 61a falls in the discharge opening 61b through the half mirror 66. The optical system 72, the entrance window 61a and the discharge opening 61b constitute a light guide section that guides light into water delivered into the treatment instrument insertion channel 26.

Furthermore, as described later, light reflected by a tissue surface and returning through the water, that is, return light enters the tank 61 from the discharge opening 61b. The half mirror 66 and an exit window 61c are arranged so that the return light from the discharge opening 61b is separated and reflected by the half mirror 66, which is a beam splitter, and advances toward the exit window 61c.

The return light exiting from the exit window 61c enters the spectroscope 65. The spectroscope 65 includes a photodetector 65a for spectral measurement.

In the present embodiment, the spectroscope 65 as a photodetection section is an apparatus that detects and outputs intensity data for each wavelength. As described later, although in the present embodiment, in the case of, for example, a white color light, the respective wavelengths included therein are measured, the photodetection section may be a photodetector that detects only a predetermined wavelength or a predetermined wavelength band, rather than a spectroscope. Even if the photodetection section is such a photodetector that detects only a predetermined wavelength or a predetermined wavelength band, whether or not a certain tissue site is different from the other tissues can be determined from the amount of the return light.

The optical system 73 such as a lens is provided so that the return light from the exit window 61c properly falls on the photodetector 65a.

Incidentally, the size of the entrance window 61a is set so that a sufficient amount of light is collected in the discharge opening 61b, that is, a larger amount of the light passing through the optical system 72 is collected. If the entrance window 61a includes, for example, a circular glass member, it is preferable that the diameter thereof have a size enabling entrance of a larger amount of light. For example, the size of an opening diameter D1 of the entrance window 61a of the tank 61 is a size according to the diameter of a beam of collected light exiting from the optical system 72.

Similarly, the size of the exit window 61c is set so that a larger amount of return light resulting from reflection by the half mirror 66 is collected by the photodetector 65a. If the exit window 61c includes, for example, a circular glass member, it is preferable that the diameter thereof have a size enabling entrance of a larger amount of light to the optical system 73. For example, the size of an opening diameter D2 of the exit window 61c of the tank 61 has a size according to the diameter of a beam of light reflected by the half mirror 66.

The control section 63 is connected to the foot switch 13, the pump 62, the light source 64, the spectroscope 65, a shutter drive section 71a that drives the shutter 71, and the monitor 52.

When an instruction signal from the foot switch 13 is inputted to the control section 63, the control section 63 controls these devices connected thereto, in order to perform an ordered cleaning operation or measurement operation. Although a detailed description is provided later, for a cleaning operation, the control section 63 controls the operation of the pump 62 so as to draw water into the tank 61 and discharge the water from the discharge opening 61b at a predetermined pressure. For a measurement operation, the control section 63 controls the operation of the pump 62 so as to draw water into the tank 61 and discharge the water from the discharge opening 61b at a predetermined pressure, and controls the operation of the light source 64, the shutter drive section 71a and the spectroscope 65 so as to perform spectral measurement of return light, and receives data from the spectroscope 65.

Before an operation of the main body apparatus 12 is described, a method for cleaning of a measurement site and a method for spectral measurement of a measurement site, which use the biological measurement apparatus 1 according to the present embodiment, will be described.

Figure 3:
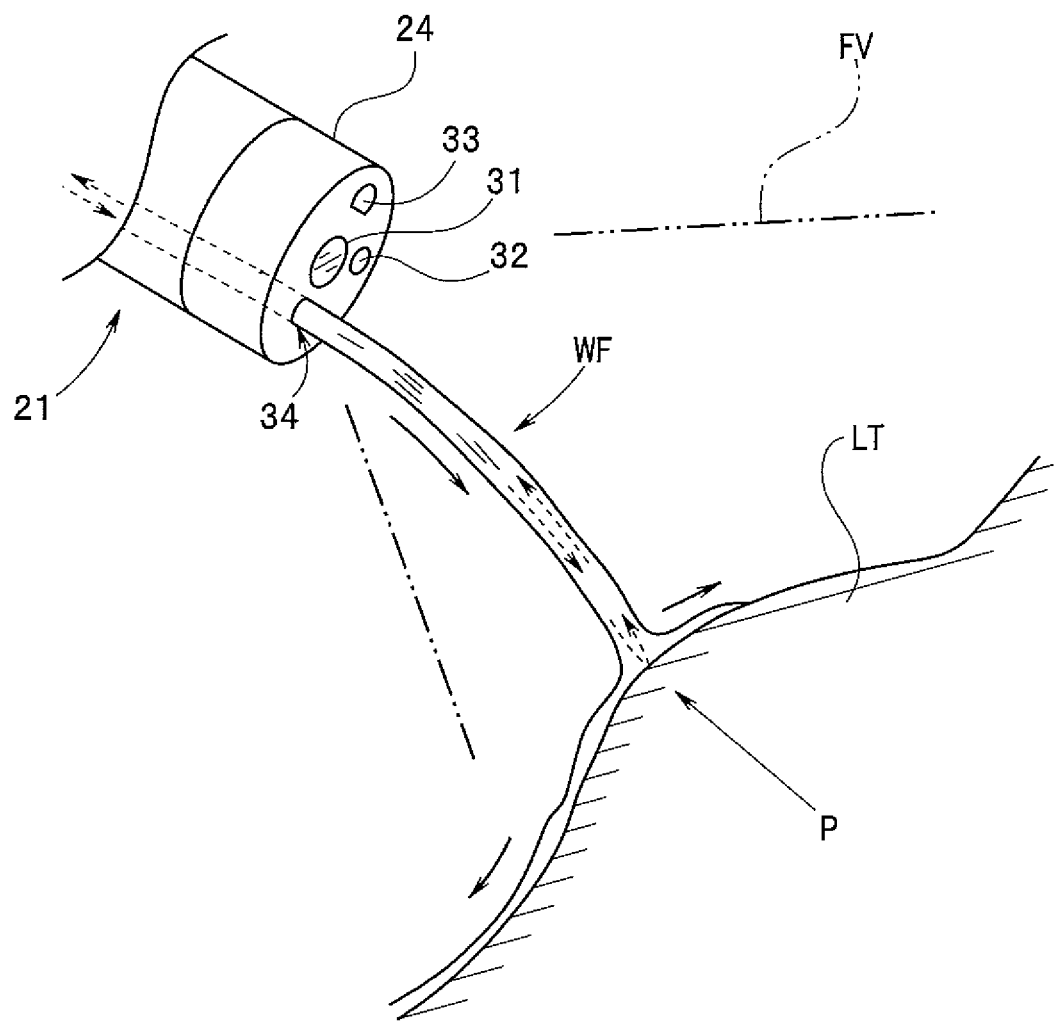
FIG. 3 is a diagram for illustrating a method for cleaning of a measurement site and a method for spectral measurement of the measurement site according to the embodiment of the present invention.

FIG. 3 is a diagram for illustrating a method for cleaning of a measurement site and a method of spectral measurement of a measurement site according to the present embodiment. A surgeon can view an image obtained by the image pickup device provided at the distal end portion by operating the endoscope 11 to insert the insertion portion 21 into, for example, a digestive tract of a subject. When a surgeon performs spectral measurement of a certain portion of a surface of a mucous membrane of a digestive tract, for example, a mucous membrane of, e.g., a stomach or a large intestine, the surgeon may wish to first clean, for example, the surface of the stomach wall.

In such case, the surgeon takes a procedure for adjusting the posture of the subject or sucking water so as to prevent a target site, which is a surface part he/she wishes to observe, from being covered by water used for cleaning at the time of spectral measurement as a result of the water being retained in the stomach. Then, the surgeon can adjust the position of the distal end portion so that water discharged from the opening portion 34 falls on the target site by operating the endoscope 11 to bend the bending portion 25 of the distal end portion, while viewing the endoscope image displayed on the monitor 42.

When the surgeon presses the pedal 13a in such state, the pump 62 is activated to deliver water in the tank 61 from the discharge opening 61b. The delivered water is discharged from the opening portion 34 through the connection tube 51 and the treatment instrument insertion channel 26. The surgeon can adjust the position of the distal end portion of the insertion portion 21 so that the water falls on the target site by operating the operation section 22 while viewing the endoscope image. The discharged water forms a water flow WF like a jet water flow, and the water flow WF falls on the target site, thereby cleaning the surface of the target site at a measurement position P. The surgeon can check the state of the cleaning by viewing the monitor 42 of the endoscope apparatus. The surgeon can stop the cleaning operation by removing the foot from the pedal 13a to turn the pedal 13a off.

For cleaning, as illustrated in FIG. 3, water discharged from the opening portion 34 of the distal end portion of the endoscope 11 exits from the opening portion 34 at a predetermined water delivery pressure and falls on the surface of a living tissue (for example, a stomach wall) LT, which is an object to be measured, forming, e.g., a parabolic shape as indicated by solid arrows. When the water flow WF like a jet water flow falls on the surface of the living tissue LT, the water flow WF moves toward a lower direction due to gravity in such a manner that the water flow WF spreads around.

Next, when the surgeon presses the pedal 13b to turn the pedal 13b on in order to perform spectral measurement of the target site, the pump 62 is activated, water in the tank 61 is discharged from the discharge opening 61, and the shutter drive section 71a is driven to open the shutter 71. The light source 64 may be in a lighted state from the point of time when the main body apparatus 12 is turned on, or may be lighted via another switch.

Also for spectral measurement, as illustrated in FIG. 3, the water is discharged from the opening portion 34 by a predetermined water delivery pressure and falls on the surface of a living tissue (for example, a stomach wall) LT, which is an object to be measured, forming the shape of, e.g., a parabola as indicated by solid arrows. Since the image pickup device is provided at the distal end portion of the endoscope 11, the surgeon can check that the water falls on the measurement site, by viewing the monitor 42. In FIG. 3, a view field range FV in which an image can be picked up by the image pickup device is indicated by alternate long and two short dashes lines.

The opening diameter of the opening portion 34 is, for example, around 2.8 to 4.0 mm, and where the endoscope insertion portion 21 has a length of around 1.5 m, the water is discharged from the opening portion 34 one to two seconds after the pressing of the pedal in the foot switch 13 although the time depends on the length of, e.g., the connection tube 51.

The pump 62 has the ability of discharging water at a predetermined pressure, and the pressure is set so that the water is discharged from the opening portion 34 of the distal end of the insertion portion 21 in the form of the water flow WF to a degree that the water is neither interrupted nor splashed. Alternatively, a pump providing such setting is selected.

Furthermore, the control section 63 controls the light source 64 and the shutter 71 so that light in a predetermined wavelength band, for example, white color light from the light source 64 exits into water through the half mirror 66. The water passes from the pump 61, through the inside of the connection tube 51 and further though the inside of the treatment instrument insertion channel 26 in the insertion portion 21 of the endoscope 11, and discharged from the opening portion 34, and thus, the light exiting into the water is reflected by the insides of the connection tube 51 and the treatment instrument insertion channel 26, which are provided with, e.g., metal coating as described above, and also reflected by the inner portion of the water flow WF delivered from the opening portion 34.

The refractive index is different between the inner walls of the connection tube 51 and the treatment instrument insertion channel 26, and water, and the light advances while being reflected by the inner walls. Also, there is air around the water flow WF discharged from the opening portion 34, which has a refractive index different from that of water, and thus, the light advances while being totally reflected by the inner portion of the delivered water flow WF.

There is air around the delivered water flow WF, and since air has a refractive index smaller than that of water, light in the water flow WF reaches the target site while being totally reflected by the boundary between the water and the air like in an optical fiber. The light reaching the target site at the measurement position P irradiates the surface of the living tissue LT of the target site and is reflected. A part of the light reflected by the surface of the living tissue LT returns into the water flow WF that is being delivered, and returns to the inside of the main body apparatus 12 while being totally reflected in the water in the treatment instrument insertion channel 26 and the connection tube 51 again. Then, spectral measurement is performed for return light returning through the water as a result of the reflection.

With the spectral measurement method according to the present embodiment, water falls on the target site also during spectral measurement, and thus, it can be considered that spectral measurement is performed while the measurement site is cleaned, in other words, together with cleaning.

Next, an operation of the main body apparatus 12 will be described according to a procedure for spectral measurement.

A surgeon inserts the insertion portion 21 of the endoscope 11 into a subject to be examined and arranges the distal end portion of the insertion portion 21 near a living tissue LT he/she wishes to perform spectral measurement of.

As described above, an image pickup device is provided at the distal end portion of the endoscope 11, enabling an image of the object to be examined to be picked up from the observation window 31, and thus, the surgeon can move the distal end portion of the endoscope 11 to the surface of the living tissue LT he/she wishes to perform spectral measurement of, while viewing an endoscope image obtained by the image pickup device, which is displayed on the monitor 42.

Then, for example, the surgeon may wish to clean the surface of the living tissue LT. In such case, the surgeon presses the pedal 13b of the foot switch 13 to turn the pedal 13b on.

Figure 4:
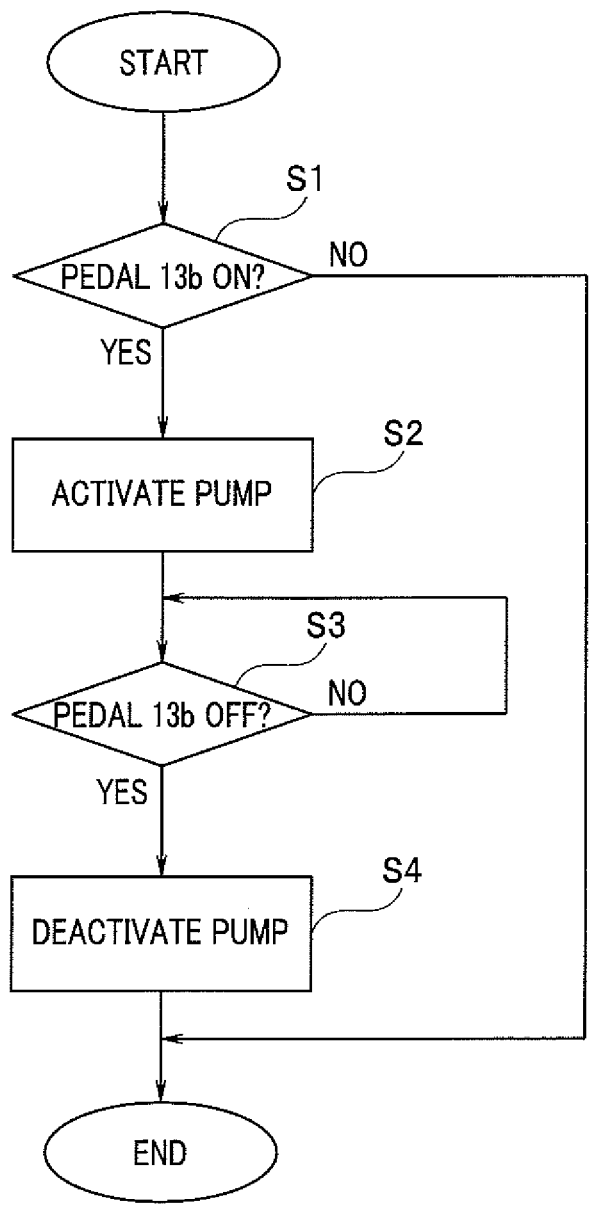
FIG. 4 is a flowchart illustrating an example of the content of processing performed by a control section 63 in the apparatus main body 12 when a cleaning mode is ordered.

When the pedal 13b is turned on, processing in FIG. 4 is performed. FIG. 4 is a flowchart illustrating an example of the content of processing performed by the control section 63 in the main body apparatus 12 when a cleaning mode is ordered.

The control section 63 determines whether or not the pedal 13b is turned on (step S1), and if the pedal 13b is not turned on, which is NO in step S1, the control section 63 performs no processing.

If the pedal 13b is turned on, which is YES in step S1, the control section 63 activates the pump 62 (step S2). Subsequently, whether or not the pedal 13b is turned off, that is, whether or not the surgeon removes the foot from the pedal 13b is determined (step S3).

If the pedal 13b is not turned off, which is NO in step S3, the control section 63 performs no processing. If the pedal 13b is turned off, which is YES in step S3, the control section 63 deactivates the pump 62 (step S4).

The surgeon can check the state of cleaning of the tissue he/she wishes to perform measurement of, while viewing an endoscope image.

When the surgeon determines that cleaning has sufficiently been performed, the surgeon performs spectral measurement. When the surgeon performs spectral measurement, the surgeon presses the pedal 13a of the foot switch 13 to turn the pedal 13a on.

Figure 5:
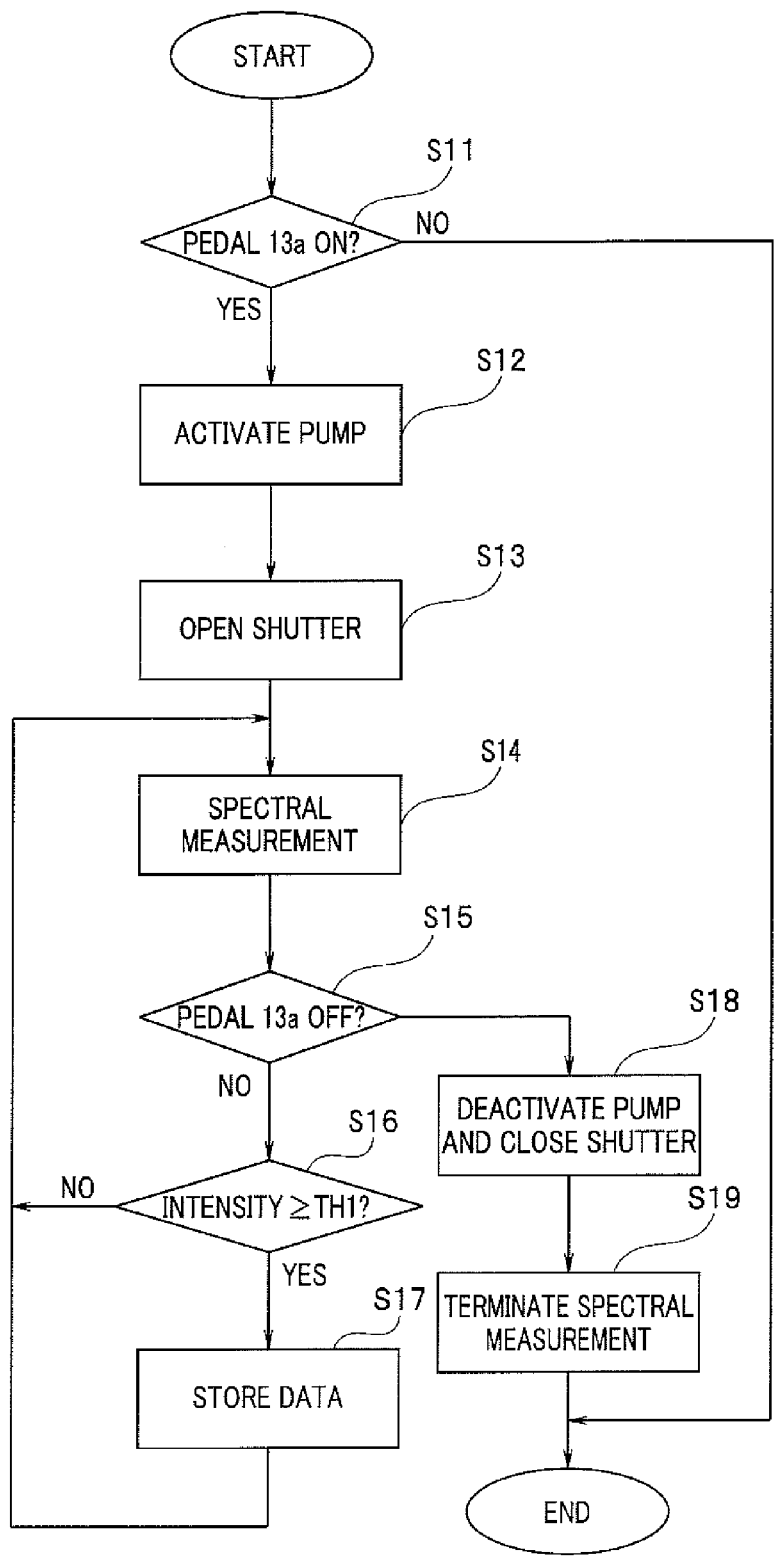
FIG. 5 is a flowchart illustrating an example of the content of processing performed by a control section 63 in the apparatus main body 12 when a spectral measurement mode is ordered.

If the pedal 13a is turned on, processing in FIG. 5 is performed. FIG. 5 is a flowchart illustrating an example of the content of processing performed by the control section 63 in the main body apparatus 12 when a spectral measurement mode is ordered.

The control section 63 determines whether or not the pedal 13a is turned on (step S11), and if the pedal 13a is not turned on, which is NO in step S11, the control section 63 performs no processing.

If the pedal 13a is turned on, which is YES in step S11, the control section 63 activates the pump 62 (step S12).

After an elapse of a predetermined set time Ts (for example one to two seconds) from the activation of the pump 62, the control section 63 outputs an activation signal to the shutter drive section 71a to open the shutter 71 (step S13).

This is because when, e.g., first spectral measurement is performed after activation of the apparatus system, time may be consumed from the activation of the pump 62 to discharge of water from the opening portion 34 after the pressing of the pedal 13a, or an distal end of the water flow WF has not reached the surface of the living tissue LT to be measured or the water flow WF may not stably fall on the surface at the beginning of discharge. Furthermore, at the beginning of discharge, the water flow WF may contain air bubbles or the water flow WF may be interrupted in the middle.

Therefore, when the pedal 13a is pressed, the control section 63 immediately activate the pump 62, and delivers water into the treatment instrument insertion channel 26, but delays timing for starting spectral measurement to be performed by the spectroscope 65 considering the time required for discharging water from the distal end of the insertion portion 21 and stabilizing the state of the water flow WF. Thus, the shutter 71 is opened the predetermined set time Ts later and guides light into the water.

After the shutter 71 is opened, the control section 63 outputs an instruction to the spectroscope 65 to start spectral measurement to detect return light (step S14).

Subsequently, whether or not the pedal 13a is turned off, that is, whether or not the surgeon removes the foot from the pedal 13a is determined (step S15).

If the pedal 13a is not turned off, which is NO in step S15, whether or not the intensity of light received by the spectroscope 65 is no less than a predetermined threshold value TH1 is determined (step S16). The content of determination processing in step S16 will be described later.

If the signal intensity is no less than the predetermined threshold value TH1, which is YES in step S16, the control section 63 stores measurement data obtained by the spectroscope 65 in the storage section 67 as a detection value (step S17).

If the light intensity is less than the predetermined threshold value TH1 (NO in step S16) or after the storage of the measurement data, the processing returns to spectral measurement processing in step S14.

If the pedal 13a is turned off, which is YES in step S15, the control section 63 deactivate the pump 62, and closes the shutter 71 (step S18) to terminate the spectral measurement (step S19).

In such a manner as described above, the surgeon can perform spectral measurement after checking the surface of a living tissue he/she wishes to perform spectral measurement of, while viewing an endoscope image.

Figure 6:
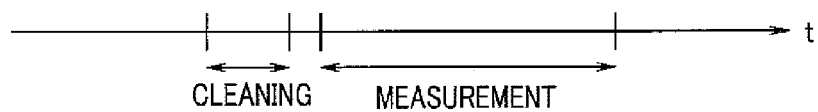
FIG. 6 is a diagram for illustrating the flow of spectral measurement according to the embodiment of the present invention.

FIG. 6 is a diagram illustrating the flow of spectral measurement. As described above, first, if necessary, the surgeon presses the pedal 13b to order cleaning processing to clean the surface of a living tissue to be measured. Next, when the surgeon presses the pedal 13a to order measurement processing, the biological measurement apparatus performs spectral measurement.

Figure 7:
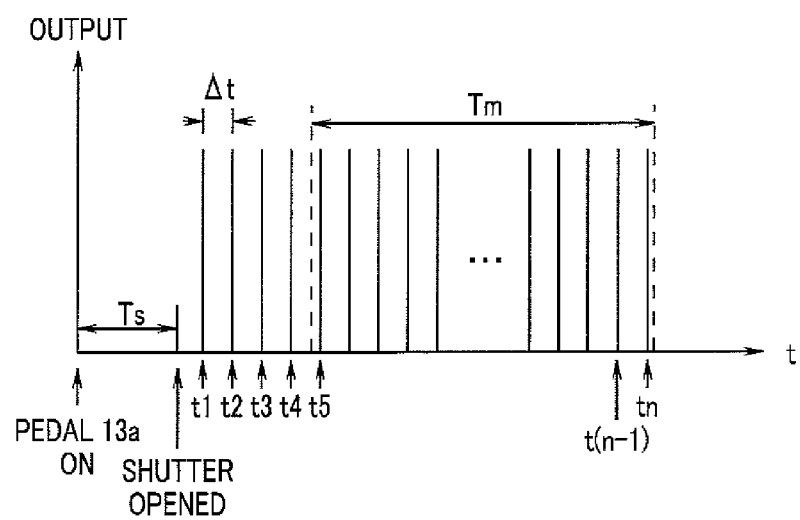
FIG. 7 is a diagram for illustrating timing for spectral measurement processing according to the embodiment of the present invention.

Next, spectral measurement processing performed by the main body apparatus 12 will be described. FIG. 7 is a diagram for illustrating timing for spectral measurement processing.

As described above, the timing for starting spectral measurement performed by the spectroscope 65 is delayed considering the time required for discharging water from the distal end of the insertion portion of the endoscope and for stabilizing the state of the water flow WF. Then, the spectroscope 65 is controlled so as to start spectral measurement after the shutter 71 is opened after the elapse of the set time Ts.

The spectroscope 65 successively perform spectral measurement at predetermined time intervals Δt, for example, 10 ms, a predetermined number of times or for a predetermined period of time (for example, 5 seconds). FIG. 7 indicates that spectral measurement is performed n times (n is a positive integer), for example, 100 times.

Return light resulting from white color light from the light source 64 being reflected by the surface of the living tissue LT through the water flow WF and returning through the water flow WF is received by the photodetector 65a. The spectroscope 65 performs spectral measurement of the light the photodetector 65a is receiving, at the time intervals Δt.

Although all data outputted by the spectroscope 65 may be used as measurement data, immediately after the start of spectral measurement, the state of the water flow WF may be unstable for any reason. For example, where the distal end of the water flow WF has not reached the surface of the living tissue LT or the water flow WF is unstable, the intensity of the return light is lowered.

Accordingly, as described in step S16, unless the value of data outputted by the spectroscope 65 is no less than the predetermined threshold value TH1, the measurement data is not stored in the storage section 67, and only data with intensity of no less than the predetermined intensity TH1 is stored in the storage section 67 as measurement data.

Figure 8:
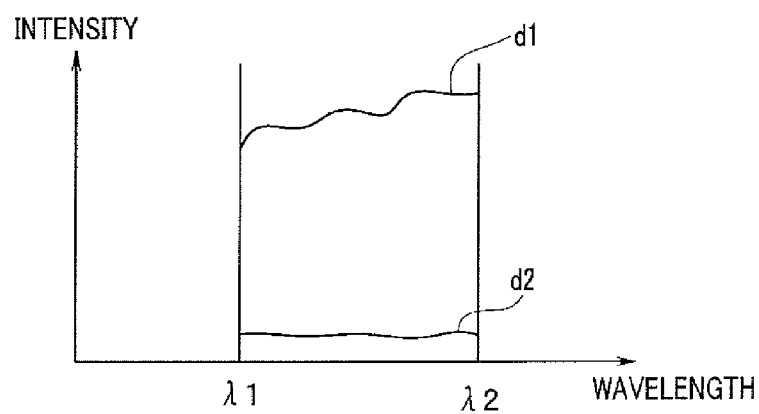
FIG. 8 is a diagram for illustrating a relationship between measurement data and a threshold value TH1 according to the embodiment of the present invention.

FIG. 8 is a diagram illustrating a relationship between measurement data and the threshold value TH1. Data outputted by the spectroscope 65 is intensity data for each wavelength. The spectroscope 65 outputs, for example, intensity data for a wavelength band the apparatus itself has or a set wavelength band. It is assumed that the wavelength band, that is, the wavelength range is a range of from a wavelength λ1 to a wavelength λ2. In the case of white color light, the range is a wavelength range of, for example, 400 to 800 nm.

For example, return light from the surface of the living tissue LT normally exhibits a wavelength distribution as indicated by distribution d1 in FIG. 8; however, if the distal end of the water flow WF has not reached the surface of the living tissue, the wavelength distribution becomes a distribution such as indicated by a distribution d2 in FIG. 8.

Therefore, the control section 63 determines in step S16 whether or not the data is used as measurement data, using expression (1) below.

$$\int_{\lambda 1}^{\lambda 2} R(\lambda) d\lambda \geq TH1 \qquad \text{Expression (1)}$$

Here, $R(\lambda)$ is the intensity of a wavelength $\lambda$. In other words, if the value of integral of the intensity of return light over a predetermined set wavelength band is no less than a predetermined threshold value, the measurement data is stored in the storage section 67 as a detection value.

Such determination as described above enables obtainment of correct spectral measurement results.

Furthermore, while expression (1) above is provided for determination in which if the value of the measurement data is excessively low, the data is not employed as measurement data, where the value of the measurement data is excessively high, also, expression (2) below can be used for determination of whether or not the data is employed as measurement data in order to determine the data to be abnormal data and prevent the data from being employed.

$$TH2 \geq \int_{\lambda 1}^{\lambda 2} R(\lambda) d\lambda \geq TH1 \qquad \text{Expression (2)}$$

Here, TH2 is a threshold value indicating an upper limit. In other words, if the value of integral of the intensity of return light over a predetermined set wavelength band is within a predetermined range, the measurement data is stored in the storage section 67 as a detection value. Such determination as described above allows obtaining more correct spectral measurements.

FIG. 7 indicates that as a result of such determination, while four pieces of data up to a time t4 are neither employed as measurement data nor stored in the storage section 67, data for a time period Tm of from a time t5 onward is stored in the storage section 67 as measurement result data.

As described above, where, e.g., the distal end of the water flow WF has not reached the surface of the living tissue or the water flow WF is in an unstable state, determination such as described above can be performed for data outputted from the spectroscope 65 to prevent improper or abnormal data from being employed as measurement data.

As described above, the biological measurement apparatus according to the present embodiment described above enables a surgeon to quickly and easily perform biological measurement.

Since the diameter of the water flow WF discharged from the opening portion 34 at the distal end of the insertion portion 21 is determined by the diameter of the opening portion 34, a surgeon may select an endoscope including an opening portion 34 having a diameter conforming to the area of a region he/she wishes to perform biological measurement of.

Next, variations of the present embodiment will be described.

(Variation of the Main Body Apparatus)

Figure 9:
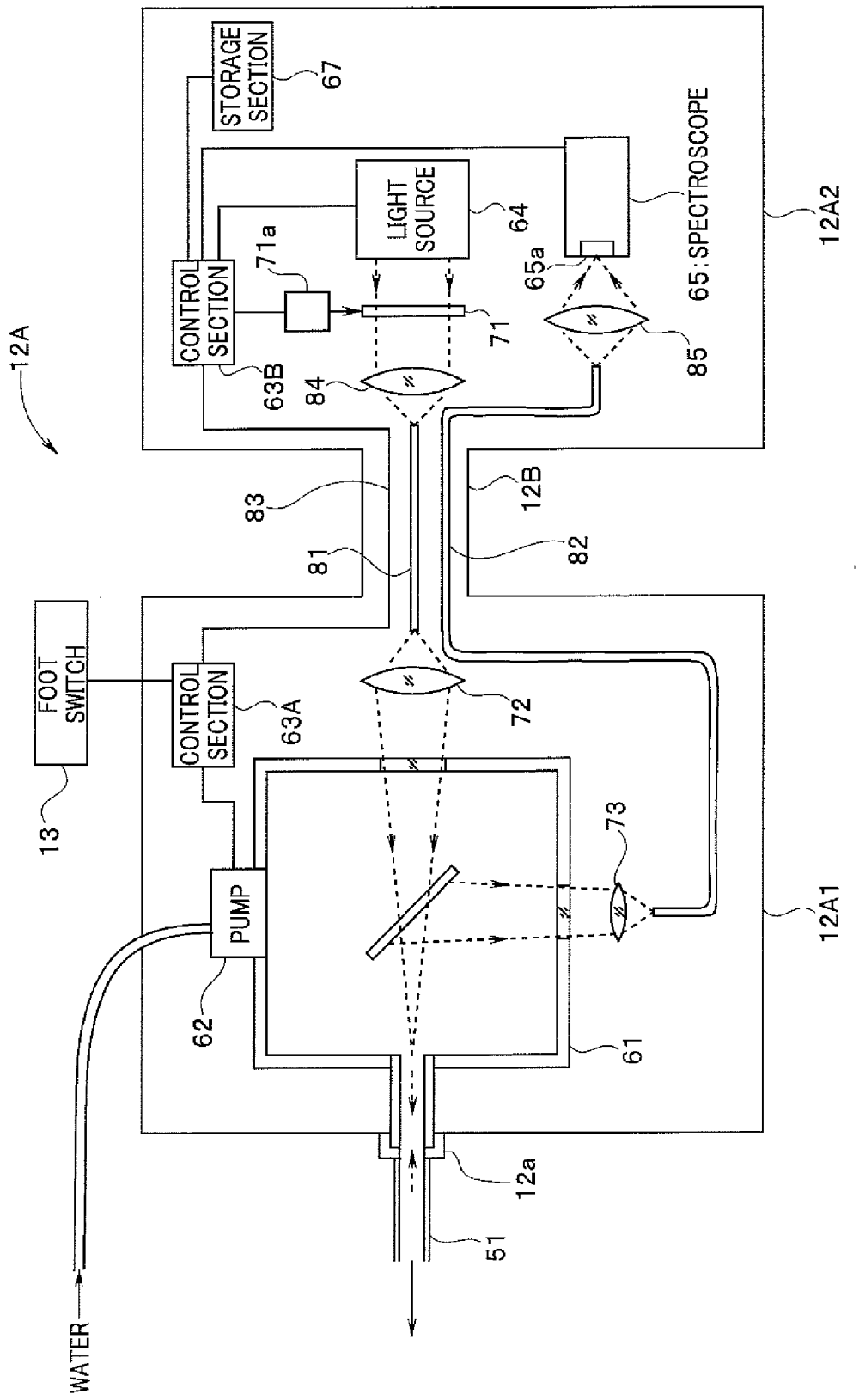
FIG. 9 is a diagram for illustrating a configuration of a variation of the main body apparatus.

FIG. 9 is a diagram illustrating a configuration of a variation of the main body apparatus. The main body apparatus in FIG. 9 includes a configuration in which a pump section and a spectral measurement section are separated from each other.

In FIG. 9, components that are the same as those in FIG. 2 are provided with same reference numerals as those in FIG. 2, and a description thereof will be omitted. A main body apparatus 12A includes: a first apparatus 12A1 including, e.g., a tank 61 and a pump 62; and a second apparatus 12A2 including, e.g., a light source 64, a spectroscope 65 and a storage section 67. The first apparatus 12A1 and the second apparatus 12A2 are connected via a connection cable 12B including two optical fibers 81 and 82 and a signal line 83.

The first apparatus 12A1 includes a control section 63A connected to the foot switch 13, the control section 63A controlling the pump 62. The second apparatus 12A2 includes a control section 63B that controls the light source 64, the spectroscope 65 and a shutter drive section 71a. The control sections 63A and 63B are connected via the signal line 83, enabling data to be exchanged with each other.

Light from the light source 64 is collected into one end of the first optical fiber 81 in the connection cable 12B by a lens 84 in the second apparatus 12A2, and exits from the other end. The optical fiber 81 and a collecting lens 72 are arranged so that irradiation with the light that has exited from the other end of the first optical fiber 81 is provided toward the collecting lens 72 in the tank 61.

Return light is collected into one end of the second optical fiber 82 by the lens 73, and exits from the other end. The optical fiber 82 and a collecting lens 85 are arranged so that irradiation of the light that has exited from the other end of the second optical fiber 82 is provided toward the collecting lens 85 for the spectroscope 65.

The control section 63A controls the pump 62 according to the operation of the foot switch 13, and controls a shutter 71 via the control section 63B. The control section 63B controls the light source 64 and the spectroscope 65, receives data outputted by the spectroscope 65, and stores measurement data in the storage section 67 after determination such as described above.

The configuration of the variation as described above enables provision of a desired system by changing only the second apparatus according to different types of light sources, spectroscopes, etc., or changing only the first apparatus according to different types of pumps, and combining the second or first apparatus with the unchanged first or second apparatus, which leads a decrease in manufacture cost in the entire system.

(Variations of the Water Delivery Tube)

Next, a variation of the water delivery tube provided in the endoscope will be described. Although in the above-described embodiment, the treatment instrument insertion channel 26 provided inside the endoscope 11 is used for a tube for liquid delivery and light conveyance, a tube provided outside the insertion portion 21 of the endoscope 11 may be used instead of the treatment instrument insertion channel.

By using a tube portion that is other than the treatment instrument insertion channel for the water delivery tube, a surgeon can make the diameter of the water flow WF having a desired size. In other words, a tube having a desired diameter or an overtube including such tube may be selected without changing the endoscope.

Figure 10:
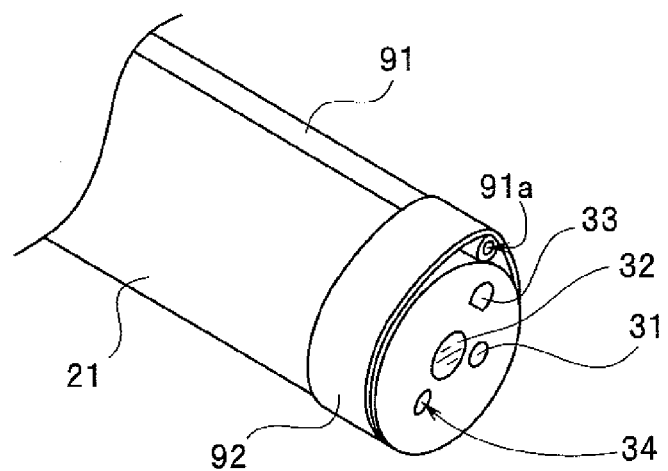
FIG. 10 relates to a variation of a conduit and is a diagram illustrating an example in which a water delivery tube is provided outside an insertion portion of an endoscope.

FIG. 10 relates to a variation of the water delivery tube and is a diagram illustrating an example in which a water delivery tube is provided outside an insertion portion of an endoscope. As illustrated in FIG. 10, a tube 91 with one end thereof connected to a water delivery connector 12a in a main body apparatus 12 is laid along an insertion portion 21, and the other end is fixed by a fixing member 92 such as a tape at a distal end of the insertion portion 21. Although FIG. 10 indicates that the tube 91 as a tube portion is fixed only at the distal end of the insertion portion 21, the tube 91 is fixed at one or more necessary positions of the insertion portion 21 by fixing members 92 such as tapes.

If a plurality of tubes 91 with different internal diameters are prepared in advance, a surgeon can select and use a tube 91 with an inner diameter according to the size of the region he/she wishes to perform spectral measurement of.

Figure 11:
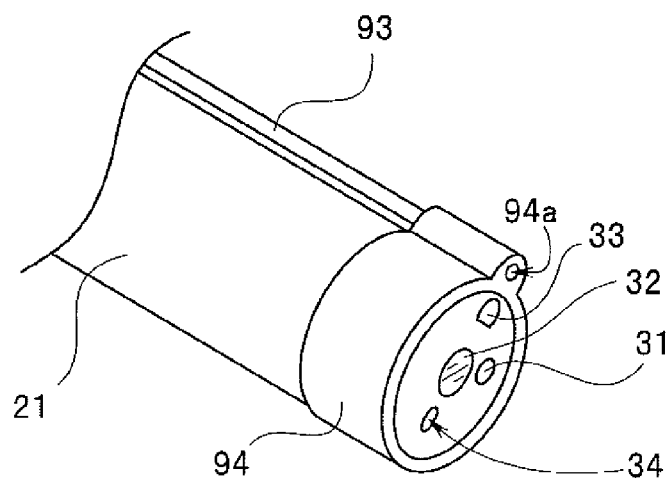
FIG. 11 relates to another variation of the conduit and is a diagram for illustrating another example in which a water delivery tube is provided outside an insertion portion of an endoscope.

FIG. 11 relates to another variation of the water delivery tube, and is a diagram indicating another example in which a water delivery tube is provided outside an insertion portion of an endoscope. As illustrated in FIG. 11, a tube 93 with one end thereof connected to a water delivery connector 12a in a main body apparatus 12 is laid along an insertion portion 21, and the other end is connected to one end of a hole 94a in a distal end cap 94 attached so as to cover an distal end of the insertion portion 21. The distal end cap 94 having an annular shape is attached to the distal end of the insertion portion 21 so as to fit on the distal end. The distal end cap 94 includes the hole 94a formed on a projection portion projecting in an outer circumferential direction thereof. The tube 93 can be attached to one end of the hole 94a, and the other end of the hole 94a is formed so as to deliver water along the axis direction of the insertion portion 21 when a water flow WF is delivered.

If a plurality of tubes 93 with different inner diameters are prepared in advance, and distal end caps corresponding to the respective tubes are prepared in advance, a surgeon can select and use a tube 93 with an inner diameter according to the size of a region he/she wishes to perform spectral measurement of.

Such configuration of the variation of the water delivery tube as described above enables a surgeon to select and use a tube according to the size of a region he/she wishes to perform spectral measurement of.

For still another variation of the water delivery tube, a water delivery tube may be provided on an overtube for the insertion portion 21, rather than fixing a water delivery tube to an outer circumferential portion of the endoscope.

Figure 12:
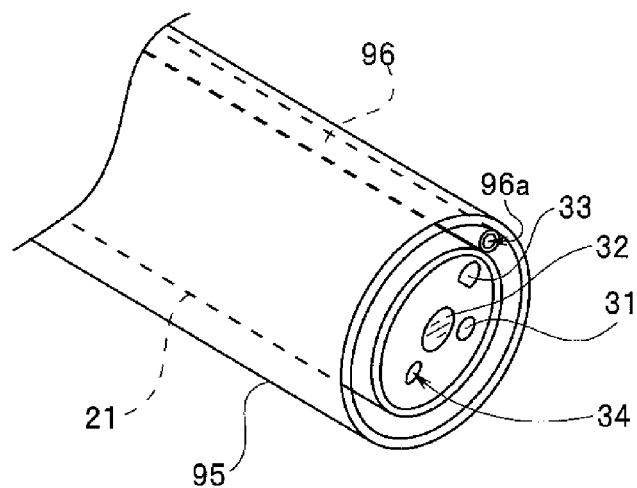
FIG. 12 relates to still another variation of the conduit and is a diagram illustrating an example in which a water delivery tube is provided in an overtube.

FIG. 12 relates to a still further variation of the water delivery tube, and is a diagram for illustrating an example in which a water delivery tube is provided on an overtube. An overtube 95, which is intended to assist insertion of an insertion portion 21 of an endoscope 11, is attached to the insertion portion 21 so as to cover the insertion portion 21. A water delivery tube 96 is fixed to an inner wall of the overtube 95.

A distal end of the water delivery tube 96 as a tube portion is fixed to a distal end of the overtube 95, and the proximal end side is connected to a water delivery connector 12a in a main body apparatus 12. A water flow FW is delivered from a hole 96a at the distal end of the water delivery tube 96.

If a plurality of tubes 96 with different inner diameters are prepared in advance, overtubes corresponding the respective tubes are also prepared in advance, a surgeon can select and use an overtube including a tube 96 with an inner diameter according to the size of the region he/she wishes to perform spectral measurement of.

(Variation of the Tank)

Next, a variation of the tank will be described. Although the shape of the above-described tank 61 has a box shape or a cylindrical shape, and including the half mirror 66 as a beam splitter therein, an integrating sphere not including a half mirror therein may be used as a tank.

Figure 13:
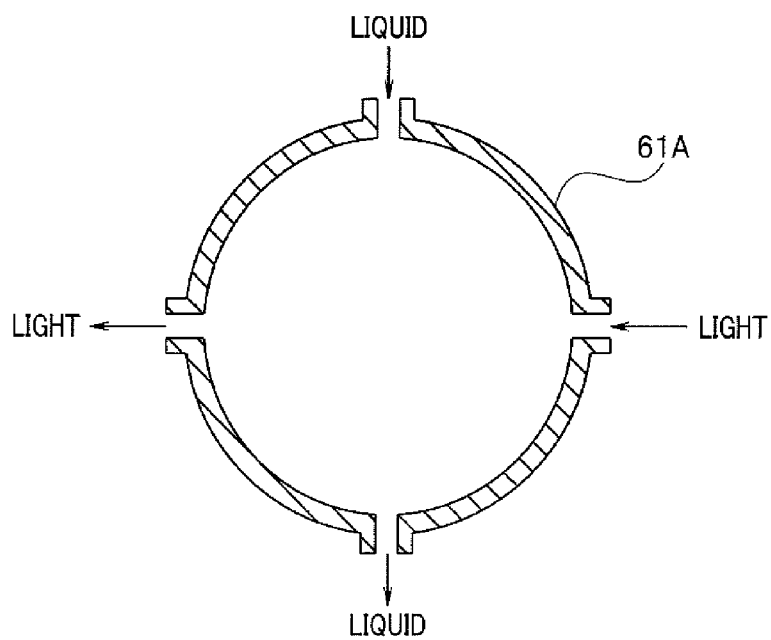
FIG. 13 is a diagram for illustrating an integrating sphere as a variation of a tank.

FIG. 13 is a diagram for illustrating an integrating sphere as a variation of the tank. An integrating sphere 61A is formed so that its inner surface reflects light, and as with the tanks illustrated in FIGS. 2 and 9, includes an entrance port for light from a light source, an exit port for light directed to a spectroscope, and an entrance port and an exit port for water, which is a liquid from a pump. The integrating sphere 61A is not necessarily has a spherical shape, and may have a rectangular parallelepiped shape. The inner surface of the integrating sphere is coated with a coating material such as barium sulfate, magnesium oxide or white color ceramics so as to reflect light well. The integrating sphere provides light separating means.

(Variation of the Pump)

Although in the biological measurement apparatus according to the above-described embodiment, water, which is a liquid as a medium that propagates light, is discharged from the tank at a predetermined pressure by the pump, water may be discharged from a tank using natural gravity, rather than using a pump. For example, a water feed tank for supplying a liquid to a tank may be arranged at a higher position relative to the position of a tank 61 to deliver water to the tank 61 or the integrating sphere 61A using the difference in gravity therebetween.

(Variation of the Light Source)

Although the above examples have been described supposing that the light source has a predetermined wavelength band, for example, as indicated by a dotted line in FIG. 2, the main body apparatus 12 may be configured so that a filter 101 that transmits only light in a desired wavelength band can be arranged between the light source 64 and the shutter 71.

Such configuration enables emission of light in a desired wavelength band by making light emitted from the light source pass through a desired filter to change the light according to the purpose of measurement.

As described above, the biological measurement apparatuses according to the embodiment of the present invention and the respective variations, which have been described above, enable quick and easy biological measurement.

Furthermore, with measurement according to the present embodiment and the respective variations, a liquid falls on a target site also during biological measurement, enabling biological measurement to be performed while cleaning the measurement site.

The present invention is not limited to the above-described embodiment, and various changes, alternations, etc., can be made without changing the spirit of the present invention.

What is claimed is:

1. A biological measurement apparatus for performing spectral measurement on a biological body, the biological measurement apparatus comprising:
   a tube portion having a distal-end opening portion and a proximal-end opening portion;
   a liquid delivery apparatus that is connected with the proximal-end opening portion of the tube portion such that light from a light source that emits light in a predetermined wavelength band enters the proximal-end opening portion, and delivers a liquid from the proximal-end opening portion into the tube portion;
   light separating means that is provided between the proximal-end opening portion and the light source, for separating light entering the proximal-end opening portion and return light which is returned through the liquid after reflection by the biological body as an object and emitted from the proximal-end opening portion, the return light resulting from reflection of the light which enters the proximal-end opening portion and is emitted from the distal-end opening portion after passing through the tube portion,
   a control section that performs a spectral measurement on the biological body based on an output of a photodetection section that detects the return light which is separated by the light separating means.

2. The biological measurement apparatus according to claim 1, wherein the tube portion is a treatment instrument insertion channel.

3. The biological measurement apparatus according to claim 1, wherein the photodetection section is a spectroscope.

4. The biological measurement apparatus according to claim 1, wherein the liquid delivery apparatus includes a pump that delivers the liquid at a predetermined pressure.

5. The biological measurement apparatus according to claim 1,
   wherein the light separating means is a beam splitter; and
   wherein the photodetector detects the return light resulting from the separation in the beam splitter.

6. The biological measurement apparatus according to claim 1,
   wherein the light separating means is an integrating sphere; and
   wherein the photodetector detects the return light resulting from the separation in the integrating sphere.

7. The biological measurement apparatus according to claim 1, comprising:
   an endoscope including the tube portion;
   a main body apparatus; and
   a connection tube connecting the tube portion and the main body apparatus,
   wherein the main body apparatus includes the liquid delivery apparatus that delivers a liquid into the tube portion via the connection tube.

8. The biological measurement apparatus according to claim 1, wherein the tube portion is provided inside or on an outside of an insertion portion of the endoscope.

* * * * *